United States Patent [19]
Ahmed et al.

[11] Patent Number: 6,103,809
[45] Date of Patent: Aug. 15, 2000

[54] THERMOPLASTIC COMPOSITIONS COMPRISING CRYSTALLINE WATER SOLUBLE POLYMERS AND AMORPHOUS WATER SENSITIVE POLYMERS

[75] Inventors: Sharf U. Ahmed; Andualem Emiru, both of Woodbury; Leslie J. Clapp, Wyoming; Mark S. Kroll, Arden Hills; Greg J. VanLith, St. Paul, all of Minn.

[73] Assignee: H.B. Fuller Licensing & Financing, Inc., St. Paul, Minn.

[21] Appl. No.: 09/195,335

[22] Filed: Nov. 18, 1998

Related U.S. Application Data

[63] Continuation-in-part of application No. 09/078,839, May 14, 1998, Pat. No. 5,869,596, which is a continuation-in-part of application No. 08/927,116, Aug. 29, 1997, Pat. No. 5,866,675, which is a continuation-in-part of application No. 08/555,524, Nov. 9, 1995, Pat. No. 5,663,286.

[51] Int. Cl.[7] .................................................... C08L 77/00
[52] U.S. Cl. ........................... 524/489; 524/487; 525/58; 525/179; 525/182; 525/425; 525/432
[58] Field of Search ................ 525/58, 432, 425, 525/179, 182, 487, 489

[56] References Cited

U.S. PATENT DOCUMENTS

| | | | |
|---|---|---|---|
| 3,882,090 | 5/1975 | Fagerburg et al. | |
| 4,217,389 | 8/1980 | Peterson | 428/383 |
| 5,053,484 | 10/1991 | Speranza et al. | 528/338 |
| 5,086,162 | 2/1992 | Speranza et al. | 528/339 |
| 5,118,785 | 6/1992 | Speranza et al. | 528/347 |
| 5,324,812 | 6/1994 | Speranza et al. | 528/338 |
| 5,393,849 | 2/1995 | Srinivasan et al. | 525/425 |
| 5,459,184 | 10/1995 | Bunnelle et al. | 524/221 |
| 5,663,286 | 9/1997 | Ahmed et al. | 528/339 |
| 5,866,675 | 2/1999 | Ahmed et al. | 528/339 |
| 5,869,596 | 2/1999 | Ahmed et al. | 528/339 |

FOREIGN PATENT DOCUMENTS

WO 96/08538  3/1996  WIPO.

*Primary Examiner*—Ana Woodward
*Attorney, Agent, or Firm*—Carolyn A. Fischer

[57] ABSTRACT

The present invention relates to a thermoplastic composition comprising at least one crystalline water sensitive polymer and at least one amorphous water sensitive polymer. The thermoplastic composition may optionally further comprise additional ingredients such as other polymers, tackifying resins, plasticizers, waxes, and mixtures thereof. The thermoplastic compositions are useful in a variety of applications wherein water or moisture sensitive thermoplastic materials are employed such as various packaging adhesive applications including case and carton sealing, remoistenable adhesives, repulpable/recyclable adhesives and multiwall bag applications. The present invention is also useful for moisture activatable reinforcement strings and opening tapes for corrugated containers, as well as for a variety of nonwoven applications such as body fluid impermeable barriers, core stabilization adhesives, and construction adhesives.

16 Claims, No Drawings

6,103,809

THERMOPLASTIC COMPOSITIONS COMPRISING CRYSTALLINE WATER SOLUBLE POLYMERS AND AMORPHOUS WATER SENSITIVE POLYMERS

RELATED APPLICATIONS

This application is a Continuation-In-Part of U.S. patent application Ser. No. 09/078,839 filed May 14, 1998, now U.S. Pat. No. 5,869,596, which is a continuation in part of U.S. patent application Ser. No. 08/927,116 filed Aug. 29, 1997, now U.S. Pat. No. 5,866,675, which is a continuation in part of U.S. patent application Ser. No. 08/555,524 filed Nov. 9, 1995, now U.S. Pat. No. 5,663,286.

FIELD OF THE INVENTION

The present invention relates to a thermoplastic composition comprising at least one crystalline water sensitive polymer and at least one amorphous water sensitive polymer. The thermoplastic composition may optionally further comprise additional ingredients such as other polymers, tackifying resins, plasticizers, waxes, and mixtures thereof. The thermoplastic compositions are useful in a variety of applications wherein water or moisture sensitive thermoplastic materials are employed such as various packaging adhesive applications including case and carton sealing, remoistenable adhesives, repulpable/recyclable adhesives and multiwall bag applications. The present invention is also useful for moisture activatable reinforcement strings and opening tapes for corrugated containers, as well as for a variety of nonwoven applications such as body fluid impermeable barriers, core stabilization adhesives, and construction adhesives.

BACKGROUND OF THE INVENTION

Several patents are directed to water soluble polyamides. U.S. Pat. No. 3,882,090 to Fagerberg et al., issued May 6, 1975 relates to linear water-soluble polyamides having ether linkages in the polymer chain. The polyamides are useful as textile sizing agents, coatings, adhesives and water soluble films.

U.S. Pat. No. 5,053,484 to Speranza et al., issued Oct. 1, 1991 relates to polyether amides produced by reacting a polyethylene glycol diamine and a first dicarboxylic acid or an ester thereof, with a polyoxyalkylene diamine of a molecular weight of at least 500 and a second dicarboxylic acid or an ester thereof.

U.S. Pat. No. 5,118,785 to Speranza et al., issued Jun. 2, 1992 relates to polyether amides produced by reacting aromatic dicarboxylic acids with tetraethylene glycol diamine. The resulting polyether amides are useful to make polymers and fiber, with unusually good water absorbency properties.

U.S. Pat. No. 5,086,162 to Speranza et al., issued Jun. 28, 1994 relates to polyether amides produced by reacting at least one polyoxyalkylene glycol diamine with at least two different carboxylic acid or esters thereof The polyamides exhibit improved water absorbency, and/or solubility in water.

U.S. Pat. No. 5,324,812 to Speranza et al., issued Jun. 28, 1994 relates to water soluble polyamides produced by reacting two different carboxylic acids with at least one low molecular weight poly(alkylene glycol) diamine and at least one relatively high molecular weight polyoxyalkylene diamine. Such water soluble polyamides are taught to be useful in hot melt adhesive formulations.

Collectively, the polyamides taught in Speranza either exhibit a high melt point, or in the case of those polyamides having lower melt points, are disadvantageous in that the polyamides tend to block once formed into an adhesive.

WO 96/08538, published Mar. 21, 1996 is directed to a remoistenable adhesive wherein the remoistenable adhesive is a hot melt consisting of a water soluble polyamide. The water soluble polyamide may be optionally combined with a tackifier or wax.

Although water soluble polyamides have been identified for use as remoistenable adhesives, such class of polymers tend to disadvantageously have a high melt point, relatively high molten viscosity and slow speed of remoistening. Attempts to reduce the melt point and viscosity by means of formulating the polyamides with conventional hot melt adhesive additives such as tackifiers and waxes often results in diminished blocking resistance. Hence, industry would find advantage in water sensitive adhesive compositions having a low viscosity, fast rate of remoistening, that also possess the desired blocking resistance.

SUMMARY OF THE INVENTION

The applicants have found that by combining crystalline water sensitive thermoplastic materials with amorphous water sensitive thermoplastic materials, the properties of the mixture exhibit a synergistic improvement. The resulting mixture exhibits improved melt processability characteristics and improved rate of moistenability with respect to a composition based on crystalline water sensitive polymer, in addition to exhibiting excellent humidity and blocking resistance.

The thermoplastic composition of the present invention comprises at least one crystalline water sensitive thermoplastic polymer blended with at least one amorphous water sensitive thermoplastic polymer. The at least one crystalline water sensitive thermoplastic material useful in the present invention is preferably a water soluble or water dispersible polyamide. The at least one amorphous water sensitive thermoplastic material useful in the present invention includes such polymers as polyvinyl alcohol (PVOH), polyvinyl pyrrolidone (PVP), polyvinyl pyrrolidone/vinyl acetate (PVP/VA), polyvinyl pyrrolidone/acrylic acid, polyoxazoline (PEOX), and preferably, linear and branched water dispersible polyesters (EASTMAN AQ), and mixtures thereof.

In a preferred embodiment, the thermoplastic composition comprises:

a) from about 10 wt-% to about 90 wt-% of at least one crystalline water sensitive thermoplastic polymer;

b) from about 10 wt-% to about 90 wt-% of at least one amorphous water sensitive thermoplastic polymer;

c) 0 to about 30 wt-% of at least one wax.

In another embodiment, the present invention relates to an improved remoistenable adhesive composition comprising:

a) from about 10 wt-% to about 90 wt-% in the adhesive of at least one crystalline water sensitive thermoplastic polymer;

b) from about 20 wt-% to about 60 wt-% in the adhesive of at least one amorphous water sensitive thermoplastic polymer;

c) 0 to about 30 wt-% in the adhesive of at least one wax.

The present invention also relates to a body fluid impermeable article comprising a body fluid permeable substrate coated with a thermoplastic composition comprising:

a) from about 10 wt-% to about 90 wt-% of at least one crystalline water sensitive thermoplastic polymer;

b) from about 10 wt-% to about 90 wt-% of at least one amorphous water sensitive thermoplastic polymer;

c) 0 to about 30 wt-% of at least one wax.

Preferably, the body fluid impermeable barrier layer or the entire article is dispersible in tap water, yet maintains its integrity in the presence of body fluids.

DETAILED DESCRIPTION OF THE INVENTION

The term "water sensitive" means soluble, dispersible and/or swellable in an aqueous environment. In the case of repulpable applications, water soluble or water dispersible materials rather than merely swellable are preferred.

The term "crystalline polymer" means those polymers which retain their rubbery elastomeric or flexible properties above the glass transition, until the melting temperature has been surpassed. Melting is also accompanied by a loss of crystalline X-ray diffraction effects.

The term "amorphous" means those materials, that as the temperature is raised, gradually give way to a soft, extensible elastomeric phase, then to a gum and finally to a liquid. No sharp transition occurs from one phase to the other.

The term "polymer" refers to a component having a Mw greater than about 3000.

The present invention is a thermoplastic composition comprising at least one crystalline ingredient and at least one amorphous ingredient. The total amount of water sensitive ingredients in the composition is at least 50 wt-%. The crystalline ingredient is a water sensitive, preferably water soluble or water dispersible thermoplastic polymer. The concentration of the crystalline polymer is a function of the percent crystallinity which can be measured by Wide Angle X-Ray Scattering methods used for waxes. In general, the crystalline water sensitive thermoplastic polymer is present in an amount ranging from about 10 wt-% to about 90 wt-%, preferably from about 15 wt-% to about 80 wt-%, more preferably from about 15 wt-% to about 75 wt-%, and most preferably from about 20 wt-% to about 60 wt-%. The ratio of crystalline water sensitive polymer to amorphous water sensitive polymer ranges from 1:2 to 2:1 and preferably is about 1:1. However, if the crystallinity of the polymer is significantly greater than 50%, for example about 70% or greater, lower concentrations of crystalline polymer may be employed. In contrast, higher concentrations are useful if the percent crystallinity is less than about 30%. The crystalline component contributes to the blocking resistance and humidity resistance as well as improves the rate of set.

One particularly preferred class of crystalline water sensitive thermoplastic polymers are water soluble polyamides. Such polyamides are the reaction product of at least one polyoxyalkylene diamine with at least one dicarboxylic acid or esters thereof.

The polyoxyalkylene glycol diamine has the formula:

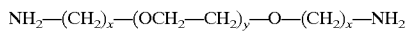

NH$_2$—(CH$_2$)$_x$—(OCH$_2$—CH$_2$)$_y$—O—(CH$_2$)$_x$—NH$_2$ wherein X ranges from 2 to 3 and Y ranges from 1 to 2.

Representative examples include triethylene glycol diamine, wherein X=2 and Y=1, and tetraethylene glycol diamine, wherein X=2 and Y=2. Commercial diamines include Jeffamine® XTJ-504 amine and Jeffamine® EDR-192 amine available from Huntsman Chemical Co., Houston, Tex. A preferred diamine is 4,7,10-trioxatridecane-1,13-diamine (TTD diamine) available from BASF, Parsippany, N.J., wherein X=3 and Y=2. Other amines such as Jeffamine® D-230, D-400, XTJ-500, XTJ-501 and XTJ-502 are also useful provided a chain terminator acid or amine is employed during the reaction, and/or additional ingredients such as waxes, tackifiers, crystalline polymers, and monoacids are subsequently combined with the reacted polyamide. For example, when adipic acid is reacted with TTD diamine and Jeffamine® D-230, the resulting polyamide is relatively slow setting with respect to reacting adipic acid with TTD diamine alone.

The polyoxyalkylene diamine is reacted with an equal stochiometric ratio of a dicarboxylic acid. Suitable dicarboxylic acids are those having from 5 to 36 carbon atoms including adipic acid, pimelic acid, azelaic acid, sebacic acid, suberic acid, dodecanedioic acid, terephthalic acid, isophthalic acid, t-butyl isophthalic acid, dimer acid and mixtures thereof. The esters and anhydrides of these acids may also be used. Adipic acid is preferred.

The resulting water soluble polyether amide preferably has a melt point about 190° C. or less as in the case when adipic acid is reacted with Jeffamine® XTJ-504. More preferably, the melt point is about 155° C. or less as in the case when adipic acid is reacted with Jeffamine® EDR-192. The most preferred water soluble polyether amide has a melt point about 150° C. or less as in the case when adipic acid is reacted with TTD diamine. This particular combination results in a faster setting, strong, easily processed water soluble polyether amide. The low melt temperature makes this combination particularly attractive for low application temperature applied remoistenable hot melt adhesives having an application temperature less than 177° C. For remoistenable adhesive, it is also preferable that the molten viscosity of the polyamide be less than about 2,000 cPs at 177° C.

The applicants have found that certain polyamides are preferred due to their contribution to the nonblocking and humidity resistant properties. Polyamides exhibiting such properties are those which are produced by reacting polyoxyalkylene diamine with at least one dicarboxylic acid or an ester thereof, the polyoxyalkylene diamine having the formula:

NH$_2$—(CH$_2$)$_3$—(OCH$_2$—CH$_2$)$_2$—O—(CH$_2$)$_3$—NH$_2$.

In this embodiment, adipic acid is the preferred dicarboxylic acid. However, other diacids may also be employed provided the mole percent of the additional diacids is about 10 mole percent or less with respect to the total acid content. When an additional diacid is employed at a concentration greater than about 10 mole percent, particularly at about 25 mole percent or greater with respect to the total diacid content, the resulting polyamide exhibits a longer set time prior to becoming completely non-blocking. Accordingly, it is often desirable to add an additional ingredient to increase the rate of set as described in further embodiments as follows.

Additionally, other water soluble polyamides contribute comparable humidity and blocking resistance provided a chain terminator is employed during the reaction and/or the polyamide is further combined with at least one additional ingredient including waxes, solid tackifiers, monocarboxylic acids, and crystalline polymers. In these embodiments, the polyamide is produced by reacting at least one polyoxyalkylene diamine with dicarboxylic acid or an ester thereof, said polyoxyalkylene diamine having the formula:

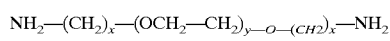

NH$_2$—(CH$_2$)$_x$—(OCH$_2$—CH$_2$)$_y$—O—(CH$_2$)$_x$—NH$_2$ wherein X ranges from 2 to 3 and Y ranges from 1 to 2.

Chain terminators include monoacids and/or monoamines and are useful in an amount less than about 5 wt-%, preferably from about 0.5 wt-% to about 2.5 wt-% based on total acid weight to control the molecular weight. Representative examples of useful monocarboxylic acids include stearic acid, benzoic acid and montannic acid such as Wax S available from Hoechst Celanese. In the absence of a chain terminator, the resulting polyamide, particularly those taught by Speranza in U.S. Pat. Nos. 5,053,484, 5,086,162, 5,324,812, and 5,118,785 are deficient in at least one property including exhibiting a high melt point, slow rate of set, high viscosity, poor humidity resistance and/or poor blocking resistance.

In addition or in the alternative, the polyamide component may be combined with at least one ingredient selected from the group consisting of waxes, tackifiers, crystalline polymers, monocarboxylic acids and mixtures thereof. The monocarboxylic acids and monoamines have been found to be useful not only as a reactant as previously described but also as an ingredient to be added after the polyamide is formed.

NP-2126 as well as other grades of water soluble or water dispersible polyamides are commercially available from H.B. Fuller Company (St. Paul, Minn.).

Although water soluble and water dispersible polyamides are the preferred water soluble crystalline material to be employed in the present invention, the applicants surmise other crystalline water sensitive polymers such as polyethylene oxide available from Union Carbide (Danbury, Conn.) and crystalline polyesters may also be suitable. Water sensitive polymers that can be synthesized to possess similar physical properties such as viscosity and extent of crystallinity to that of the exemplary polyamides are believed to be particularly useful.

In addition to the water sensitive crystalline component, the thermoplastic composition of the present invention comprises at least one amorphous water sensitive thermoplastic polymer. The amorphous water sensitive thermoplastic polymer is present in an amount ranging from about 10 wt-% to about 90 wt-%, preferably from about 15 wt-% to about 80 wt-%, more preferably from about 15 wt-% to about 70 wt-%, and more preferably from about 15 wt-% to about 60 wt-%. The concentration of amorphous water sensitive polymer employed is a function of molecular weight and glass transition temperature (Tg). In general, higher amounts of amorphous polymers may be employed when the amorphous polymer selected has a relatively high Tg, for example from about 15–20° C., or greater. In contrast, lower concentrations of amorphous polymers are employed when the amorphous polymer selected has a relatively low Tg, for example less than 0° C. For high molecular weight amorphous polymers, those having a Brookfield molten viscosity greater than about 50,000 cPs, generally lower amounts of amorphous polymer are employed, whereas higher amounts are useful for low molecular weight polymers. The amorphous water sensitive material increases the speed of remoistening and improves the bond strength to the extent that full-fiber tearing bonds are achieved both initially and maintained thereafter.

Amorphous water sensitive thermoplastic polymers contemplated for use in the present invention include such polymers as polyvinyl alcohol (PVOH) available from Nippon Grohsei (Japan) such as GROHSERAN L-301 and GROHSERAN L-302 and UNITIKA available from Unitaka Ltd. (Japan); polyvinyl pyrrolidone (PVP) available from BASF (Mount Olive, N.J.) and ISP (Wayne, N.J.); polyvinyl pyrrolidone/vinyl acetate copolymer (PVP/VA) and polyvinyl pyrrolidone/acrylic acid such as ACRYLIDONE, both available from ISP; polyethyloxazoline available from The Dow Chemical Company (Freeport, Tex.) under the tradename PEOX and from PCI Incorporated (Tucson, Ariz.) under the tradename AQUAZOL, polyvinyl methyl ether available from Amoco Chemical Co. under the tradename AMOBOND, linear polyesters, polyacrylamide and preferably water dispersible polyesters and copolyesters (EASTMAN AQ) and amorphous water soluble and water dispersible polyamides.

One particularly preferred class of amorphous water sensitive thermoplastic polymers is water dispersible polyesters and copolyesters available from Eastman Chemical Company (Kingsport, Tenn.) under the tradename EASTMAN AQ. These water dispersible polymers are linear polyesters or branched copolyesters containing sulfonomer. Such polymers are saline and body fluid insoluble, yet dispersible in tap water. The Tg of the branched water dispersible copolyesters ranges from about –5° C. to 7° C., whereas the linear polyesters have a Tg from about 30° C. to about 60° C. Commercial examples of solid thermoplastic linear water dispersible polyesters include AQ 35S (7,000 Mn), AQ 38S (10,000 Mn), and AQ 55S(8,000 Mn).

Preferred water dispersible copolyesters are those which are branched and exhibit an intrinsic viscosity of about 0.6 IV (EASTMAN AQ-14000) or less, more preferably about 0.4 IV (EASTMAN AQ-1950) or less, even more preferably about 0.3 IV (EASTMAN AQ-1350) or less, and most preferably, particularly for low application temperature remoistenable adhesives, 0.2 IV (EASTMAN AQ-1045) or less. In terms of molten viscosity, these ranges correlate to a Brookfield viscosity ranging from about 5,000 to about 40,000 cPs. Higher viscosity versions may also be employed for compositions intended for applications where a low molten viscosity is not required such as for reinforcement tapes and strings as well as fibers. Information relating to the chemical synthesis of the branched polyesters may be found in U.S. Pat. Nos. 5,543,488 and 5,552,495, incorporated herein by reference. Lighter color and low odor modifications of such water dispersible copolyester are also contemplated, particularly for nonwoven applications in which odor and color tend to be important characteristics.

The thermoplastic composition of the present invention also preferably comprises a wax in an amount up to about 30 wt-%, more preferably at an amount ranging from about 3 wt-% to about 20 wt-%, and most preferably from about 5 wt-% to about 15 wt-%. Waxes useful herein are preferably polar in nature. Polar waxes are those which contain at least one polar functional group such as hydroxyl, amide, sulfone, phosphate, sulfonamide, urethane, carboxylate acid, amine, and carbonate. The concentration of the functional group is present in an amount greater than about $2 \times 10^{-3}$ equivalents per gram and preferably greater than $3.5 \times 10^{-3}$ equivalents per gram. The molecular weight of waxes ranges from about 200 g/mole to about 1000 g/mole. Representative examples including 12-hydroxystearamide, N-(2-hydroxy ethyl 12-hydroxystearamide and N,N' ethylene bis 12-hydroxystearamide (PARICIN 220 and PARICIN 285 respectively, from CasChem, Bayonne, N.J.), stearamide (KEMAMIDE S from Witco, Memphis, Tenn.), glycerin monostearate, sorbitan monostearate, and 12-hydroxy stearic acid. Also useful alone or in combination with the above are less polar waxes such as N,N'-ethylene-bis stearamide (KEMAMIDE W-40 from Witco), linear aliphatic long chain alcohols (UNILIN 425 from Petrolite, Tulsa, Okla.), hydrogenated castor oil (castor wax), oxidized synthetic waxes, and functionalized waxes such as oxidized homopolymers and oxidized polyethylene waxes (PETROLITE E-1040). The Applicants have found that polar waxes having a melt point greater than 70° C., preferably greater than about 110° C., and more preferably about 140° C. or greater, are particularly advantageous.

The thermoplastic composition of the present invention also preferably comprises a plasticizer in an amount up to about 10 wt-% and preferably in an amount ranging from about 1 wt-% to about 5 wt-%. Surprisingly, as little as about 3 wt-% of plasticizer improves the compatibility of the ingredients. Preferred compatible plasticizers include natural and polar liquid plasticizers including phthalate plasticizers such as dioctyl phthalate and butyl benzyl phthalate (e.g., SANTICIZER 160 from Monsanto, St. Louis, Mo.); liquid polyesters such as DYNACOL 720 from Hüls and liquid polymeric plasticizer available from CP. Hall, Chicago, Ill.; benzoate plasticizers such as 1,4-cyclohexane dimethanol dibenzoate (e.g., BENZOFLEX 352 from Velsicol, Rosemont, Ill.), diethylene glycol/dipropylene glycol dibenzoate (e.g., BENZOFLEX 50 from Velsicol), dipropylene glycol dibenzoate (e.g., BENZOFLEX 9-88 from Velsicol), polypropylene glycol dibenzoate (e.g., BENZOFLEX 400 from Velsicol), and diethylene glycol dibenzoate where the mole fraction of hydroxyl groups which have been esterified ranges from 0.5 to 0.95 (e.g., BENZOFLEX 2-45 High Hydroxyl also from Velsicol); phosphite plasticizers such as t-butyl diphenyl phosphate (e.g., SANTICIZER 154 from Monsanto); polyethylene glycol having a molecular weight below about 1000 and derivatives of polyethylene glycol including PYCAL 94, the phenyl ether of PEG available from ICI (Wilmington, Del.); ethoxylated bis phenol A (e.g., MACOL 206 EM from PPG Industries, Pittsburgh, Pa.); dionyl phenol ethyoxylates (e.g., Surfonic DNP from Huntsman Chemical Corp.); liquid rosin derivatives having Ring and Ball softening points below about 60° C. such as methyl ester of hydrogenated rosin (e.g., HERCOLYN D from Hercules, Wilmington, Del.); as well as vegetable and animal oils such as glycerol esters of fatty acids and polymerizable products thereof. Preferred plasticizers include phenyl ether of PEG, butyl benzyl phthalate, toluene sulfonamide (UNIPLEX 214 from Unitex Chemical Corp, Greensboro, N.C.), acetyl-tributyl citrate (CITROPLEX A-4, Moreflex Inc, Greensboro, N.C.), benzoate plasticizers such as 1,4-cyclohexane dimethanol dibenzoate, diethylene glycol/dipropylene glycol dibenzoate, and diethylene glycol dibenzoate where the mole fraction of hydroxyl groups which have been esterified ranges from 0.5 to 0.95.

A variety of other polymers, tackifiers and additives such as antioxidants (IRGANOX 1010), pigments and fillers, particularly hydrophilic fillers such as starch or cellulose esters and acetates, may be employed in an amount up to about 10 wt-% provided such materials do not detract from the humidity resistance, blocking resistance and speed of moistenability contributed by the blend of crystalline water sensitive polymer with amorphous water sensitive polymer.

The composition of the present invention may further comprise additional thermoplastic polymers. Such polymers may be amorphous or crystalline and need not be water sensitive. Representative examples include ethylene-vinyl acetate copolymers containing about 12% to about 50% vinyl acetate, ethylene acrylic acid, ethylene methyl acrylate and ethylene n-butyl acrylate copolymers as well as polylactide, caprolactone polymers, and poly (hydroxybutyrate/hydroxyvalerate), polyvinyl alcohol, linear saturated polyesters such as DYNAPOL or DYNACOLL polymers from Creanova Inc, (Piscataway, N.J.), poly(ethylene oxide)polyether amide and polyester ether block copolymers available from Elf Atochem (Birdsboro, Pa.) as PEBAX or Hoechst Celanese (Dallas, Tex.) as RITE-FLEX respectively, and polyamide polymers such as those available as (UNIREZ) from Union Camp (Savannah, Ga.), Hüls as VESTAMELT or EMS-Chemie, Sumter, S.C. as GRILTEX).

The thermoplastic composition of the present invention may comprise tackifying resins. The tackifying resins useful herein are generally polar in nature and have a Ring & Ball softening point greater than 60° C. and include any compatible resins or mixtures thereof such as natural and modified rosins such as gum rosin, wood rosin, tall oil rosin, distilled rosin, hydrogenated rosin, dimerized rosin, and polymerized rosin; rosin esters such as glycerol and pentaerythritol esters of natural and modified rosins such as, for example, the glycerol ester of pale, wood rosin, and the glycerol ester of hydrogenated rosin, the glycerol ester of polymerized rosin, and the pentaerythritol ester of hydrogenated rosin, and the phenolic-modified pentaerythritol ester of rosin; phenolic modified terpene or alpha methyl styrene resins as well as the hydrogenated derivatives thereof such as the resin product resulting from the condensation in an acidic medium of a bicyclic terpene and a phenol.

Representative examples of preferred tackifiers include FORAL NC, KRISTALEX and ENDEX available from Hercules (Wilmington, Del.); non-ionic materials such as FORAL AX also from Hercules, alpha methyl styrene phenolics such as URATAK 68520 from DSM Resins (Panama City, Fla.), rosin esters such as UNITAC R100L available from Union Camp, terpene phenolic tackifiers such as NIREZ 300 and NIREZ V2040 available from Arizona Chemical (Panama City, Fla.).

The Applicants have found that by employing a blend of amorphous and crystalline water sensitive materials, a synergistic improvement in the adhesive performance is achieved. In general, the blocking and humidity resistance is improved by the presence of the crystalline component, whereas the rate of remoistening is enhanced by the presence of the amorphous component. In the preferred embodiments the blocking and humidity resistance is comparable to a composition based on crystalline water sensitive polymer alone.

The thermoplastic composition of the present invention is useful for a variety of applications including packaging adhesive applications such as case and carton sealing, remoistenable adhesives, repulpable/recyclable adhesives and multiwall bag applications; moisture activated reinforcement strings/tapes and opening tapes for corrugated containers; as well as for a variety of nonwoven applications such as for body fluid insoluble barrier film layers, core stabilization adhesives, construction adhesives for bonding nonwoven, absorbent(s) and films and super absorbent fixation.

The terminology "remoistenable" adhesive arose from the fact that the first classes of adhesives that were used in this fashion were water-based. The adhesive was applied to an envelope, stamp, packing tape, sticker or label, in an aqueous form and dried, resulting in a non-tacky adhesive layer. Subsequently, the adhesive was activated by remoistening the adhesive. Several of these water-based adhesives have been replaced by water or moisture activatable hot melt adhesives. In contrast, the hot melt adhesives are applied molten. Although technically the adhesive is not remoistened, in that the adhesive was never "wet" in the first place, these applications continue to be described as remoistenable adhesive applications.

For remoistenable applications, the thermoplastic composition preferably has the following properties:

| | |
|---|---|
| Brookfield Viscosity | <2,000 cPs at 350° F. (177° C.) and <1,000 cPs at 350° F. (177° C.) for low application temperatures |
| Rate of Remoistening | <30 seconds |
| Bond Strength | 100% fiber tear |
| Blocking @ Room Temperature | Good |
| Blocking at 90% RH/85° F. (29° C.), preferably at 90% RH/100°F. (38° C.) | Good |

The adhesive compositions of the present invention are repulpable making them amenable for bonding recyclable paper and corrugated for labeling, case and carton sealing applications as well as paper recyclable bags such as multi-wall bags and "beater bag" end-sealing applications. Beater bags are large paper bags filled with additives used in the paper manufacturing industry. The entire bag is added to the pulp mixture slurry when making paper.

The thermoplastic composition of the present invention is also useful as a reinforcement string as well as for tear opening tape systems for corrugated packages or cartons. These types of tapes or strings currently comprise a hydrophobic hot melt adhesive. The tapes or strings are positioned between the layers of corrugated material and then heat activated, to secure them in place. The temperature and duration of time the corrugated materials are exposed to heat varies greatly with each converter. Therefore, a wide variety of tapes and strings are needed wherein the open time, melt temperature, and viscosity of the hot melt adhesives is tailored for the specific needs of the converter. The present invention provides a "universal" string or tape that is moisture activated rather than heat activated eliminating the need to produce a wide variety of tapes and strings. The thermoplastic composition of the present invention is applied to a fiber substrate core comprising such materials as rayon, polyester and cotton as well as other synthetic and natural fibers. Depending on the dimensions of the core, a tape or string is produced. The tape or string can advantageously be wound up into a roll-good, due to the excellent humidity resistance and blocking resistance provided by the polyamide. During the conversion of paper board into corrugated containers residual moisture is driven off. The residual moisture rather than the heat activates the adhesive, adhering the tape or string in place. In case of reinforcement tapes or strings or "tear tape opening systems" as described in U.S. Pat. No. 5,098,757, incorporated herein by reference, the properties of the moisture activatable thermoplastic composition are surmised to be near the same as for the remoistenable adhesive composition with the exception that a wide range of molten viscosities are tolerable, ranging from about 1,000 cPs to about 30,000 cPs at 177° C., and preferably from about 4,000 cPs to about 30,000 cPs.

The present invention is also useful for a variety of nonwoven applications, the subject matter of copending patent application Ser. No. 08/562,038 which corresponds to EP Serial No. 96/118466.0, published Jul. 2, 1997, incorporated herein by reference. Nonwoven applications include forming a (body) fluid impermeable barrier layer by coating the thermoplastic composition of the present invention onto a carrier material such as nonwoven or paper; construction applications wherein a nonwoven, film, elastomeric, material, or absorbent is bonded to at least one other substrate by means of an adhesive; core stabilization wherein adhesive is applied to fibrous pulp to enhance the tear strength or wet strength of the pulp, and superabsorbent polymer fixation wherein particles of SAP are bonded to a substrate. The formation of films in-line by coating a substrate with the inventive thermoplastic composition is of particular interest for manufacturing flushable absorbent disposable products such as sanitary napkins. The thermoplastic composition may be used to form a continuous film in a single application by non-contact slot coating of the inventive thermoplastic composition or by multiple applications. To reduce costs, preferably the composition is coated at low basis weight ranging from about 10 g/m$^2$ to about 50 g/m$^2$ and more preferably from about 10 g/m$^2$ to about 25 g/m$^2$. Alternatively, due to the water solubility of embodiments of the present invention, the composition can be dispersible in water and coated onto a water permeable substrate in aqueous form. A variety of disposable articles can be formed including disposable diapers and training pants, adult incontinent devices, sanitary napkins and pantiliners, surgical drapes and gowns, and the like. For flushable articles, the thermoplastic composition is preferably tap water soluble, yet body fluid insoluble.

The invention is further illustrated by the following non-limiting examples:

EXAMPLES

Test Methods:

1. Melt Viscosity is determined in accordance with the following procedure using a Brookfield Laboratories DVII+ Viscometer in disposable aluminum sample chambers. The spindle used is a SC-27 hot-melt spindle, suitable for measuring viscosities in the range of from 10 to 100,000 centipoise. The sample is placed in the chamber, which is in turn inserted into a Brookfield Thermosel and locked into place. The sample chamber has a notch on the bottom that fits the bottom of the Brookfield Thermosel to ensure that the chamber is not allowed to turn when the spindle is inserted and spinning. The sample is heated to the desired temperature, with additional sample being added until the melted sample is about 1 inch (2.5 cm) below the top of the sample chamber. The viscometer apparatus is lowered and the spindle submerged into the sample chamber. Lowering is continued until brackets on the viscometer align on the Thermosel. The viscometer is turned on, and set to a shear rate which leads to a torque reading in the range of 30 to 60 percent. Readings are taken every minute for about 15 minutes, or until the values stabilize, which final reading is recorded.

2. Blocking Resistance is determined by preparing a coating on a sheet of 20 lbs. (9 kg) bleached Kraft paper (standard copy paper) with the thermoplastic composition at a thickness ranging from about 0.6 to 1 mil (0.002 cm to 0.003 cm) using a suitable coating device or draw-down technique. The coated paper is then cut into 1 inch (2.5 cm) strips and conditioned at 50% relative humidity for two hours. At least three strips of the coated paper are placed on a tray and a piece of paper placed on top, sandwiching the thermoplastic composition between two paper layers. A 500 g weight is place on top of each strip resulting in a force of 500g/sq. inch and the tray is placed in a 140° F. (60° C.) oven for 24 hours. After 24 hours, the uncoated paper is removed noting the extent of thermoplastic composition sticking or picking to the uncoated paper. The extent of blocking is characterized as follows:

"excellent"—no picking, paper falls from polyamide without resistance

"good"—the uncoated paper must be removed by hand and exhibits very slight picking "pass"—the uncoated paper must be removed by hand and exhibits significant picking, but no fiber tear "blocked"—the uncoated paper must be removed by hand and exhibits fiber tear 3. Humidity Resistance is tested in the same manner as blocking resistance with the exception that the test is conducted at 38° C. and 90% relative humidity for 24 hours.

4. Rate of Remoistening & Bondability First a hot melt adhesive sample and metal draw down bar are heated in an oven at 165° C. Once melted, a 0.5 to 1.0 mil (0.001 cm to 0.003 cm) film is applied to a paper substrate that is taped onto the laboratory benchtop. After cooling, the adhesive thickness of each coated sheet of paper is measured to ensure the film thickness falls between 0.5 and 1.0 mils (0.001 cm and 0.003 cm) thickness and is then cut into ½ inch (1.3 cm) strips. Next, a ½ inch (1.3 cm) coated strip is moistened with an applicator containing room temperature water and immediately pressed onto a second piece of bond paper with medium finger pressure (as you would seal an envelope). Immediately the stop watch is started to measure the length of time elapsed from the point a coated strip is pressed onto bond paper until it is removed. When the coated strip is removed from the bond paper, the stop watch is stopped and the elapsed time and percent fiber tear is recorded.

The rate of remoistening is determined to be the length of time it takes a hot melt adhesive to develop a fiber tearing bond. The percent fiber tear is also recorded.

5. Rate of Set

Molten adhesive ranging in temperature from about 160° C. to about 177° C. is drawn down onto a paper substrate at a thickness of 0.5 mil (0.001 cm). The film is evaluated by cautiously contacting the film with ones fingertips immediately after being drawn. A "fast setting" composition is tack-free in about one second or less, whereas a slow setting composition takes longer to become tack-free.

Comparative Examples A and B comprises NP-2126, a polyamide commercially available from H.B. Fuller Company (St. Paul, Minn.) in combination with wax. Although this product has good blocking resistance, it tends to remoisten slowly. After a 50 second dwell time, only 60% fiber tear is achieved for Comparative Example A and 80% fiber tear after 45 seconds for Comparative Example B. In order to achieve 100% fiber tear, a dwell time of 120 seconds is required. Additionally, these products suffer by virtue of the fact that after 24 hours, adhesive transfer is evident rather than full-fiber tearing bonds.

In contrast, Comparative Examples B and C comprise Eastman AQ-1045, a 0.21V water dispersible copolyester in combination with wax. Although this product has a fast rate of moistenability, i.e., forming a full-fiber tearing bond (100% FT) within 30 seconds, this product blocks at room temperature and at 90%RH/38° C.

Examples 1–4 represent thermoplastic compositions of the present invention. One would expect to achieve properties intermediate between the properties of a composition based solely on crystalline water sensitive polymer (A and B) and that of a composition based solely on amorphous water sensitive polymer (C and D). However, unexpectedly, the blocking tendencies of the copolyester are completely diminished without any compromise of the rate of bond formation.

TABLE 1

| Ingredient Trade Name WT-% | A | B | C | D | Example 1 | Example 2 | Example 3 | Example 4 |
|---|---|---|---|---|---|---|---|---|
| AQ-1045 | | | 87 | 82 | 44.5 | 42 | 27 | 57 |
| NP-2126 | 87 | 82 | | | 42.5 | 40 | 60 | 30 |
| Paricin 285 | 10 | 10 | 10 | 10 | 10 | 10 | 10 | 10 |
| Paricin 220 | | 5 | | 5 | | 5 | | |
| Benzoflex 9-88 | 2.5 | 2.5 | 2.5 | 2.5 | 2.5 | 2.5 | 2.5 | 2.5 |
| Irganox 1010 | 0.5 | 0.5 | 0.5 | 0.5 | 0.5 | 0.5 | 0.5 | 0.5 |

| PROPERTIES | | | | | | | | |
|---|---|---|---|---|---|---|---|---|
| Rate of Remoistening & Bondability | | | | | | | | |
| Initial - % Fiber Tear/Time | 60/50 sec | 80/45 sec | 100/30 sec | 100/30 sec | 100/30 sec | 100/30 sec | 100/30 sec | 100/30 sec |
| After 24 hrs (% FT) | transfer | transfer | 100 | 95 | 10 | 95 | 10 | 100 |
| Blocking Resistance | | | | | | | | |
| At room temperature | Good | Good | Blocked | Good | Good | Good | | |
| 90% RH/38 C. | Good | Good | Blocked | Blocked | Good | Good | Good | Good |
| Rate of Set | Fast | Fast | Fast | Fast | Fast | Fast | Fast | Fast |
| Viscosity @ 163° C. (cps) | 755 | 572 | 2670 | 1255 | 1407 | 1005 | | |

60

TABLE 2

| Ingredient Trade name Wt-% | E | Example 5 | Example 6 | Example 7 | Example 8 | Example 9 |
|---|---|---|---|---|---|---|
| Gohseran L-301 | 75 | 44.5 | 25 | | | |
| Glycerine | 12.5 | | | | | |
| 12 Hydroxy stearic acid | 12.5 | | | | | |
| NP-2126 | | 42.5 | 65 | 40 | 40 | 40 |
| Paricin 285 | | 10 | | | | |
| Benzoflex 9-88 | | 2.5 | 10 | | | |
| Irganox 1010 | | 0.5 | | | | |
| R-219 | | | | 60 | | |
| Eukaline 480 | | | | | 60 | |
| HL-9449 | | | | | | 60 |
| PROPERTIES | | | | | | |
| Rate of Remoistening & Bondability | | | | | | |
| Initial - % Fiber Tear/Time | | 90/30 sec | | 75/30 sec | 90/30 sec | 90/30 sec |
| After 24 hrs (% FT) | 80/30 sec | 90%+ | 90/30 sec | 90%+ | ~40% | 90%+ |
| Blocking Resistance | | | | | | |
| At room temperature | Tacky | Good | Good | Good | Good | Good |
| 90% RH/38 C. | Blocked | Good | Good | Good | Good | Good |
| Rate of Set | Fast | Fast | Fast | Fast | Fast | Fast |

Table 2 depicts an additional comparative example and further examples of the present invention employing other amorphous water sensitive polymers. Comparative Example E represents a water sensitive hot melt adhesive composition based on polyvinyl alcohol. Comparative Example E is slightly tacky at room temperature and blocks at conditions of 90% relative humidity and 38° C. Examples 5 and 6 employ a crystalline water sensitive polyamide in combination with the amorphous polyvinyl alcohol, eliminating the poor blocking resistance. R-219 available from Moore Response (Green Bay, Wis.), Eukalin 480 available from Hunkeler Corporation (Marietta, Ga.) and HL-9449 available from H.B. Fuller Company represent commercially available remoistenable hot melt adhesives. The R-219 and Eukaline 480 are based on polyvinyl pyrrolidone/vinyl acetate, whereas the HL-9449 is based on polyethyloxazoline. All three of these products were found to block at conditions of 70% relative humidity and 25° C. However, upon blending these products with a crystalline water sensitive polymer the blocking resistance is significantly improved.

TABLE 3

| Ingredient Trade name Wt-% | Example 10 | Example 11 | Example 12 | Example 13 |
|---|---|---|---|---|
| NP-2126 | 70 | 62.5 | 75 | 75 |
| AQ 35S | 17 | 27 | 14.2 | 14.2 |
| Paricin 285 | 10 | 5 | 5 | 5 |
| Benzoflex 352 | | | 5 | |
| Benzoflex 400 | | | | 5 |
| Benzoflex 9-88 | 2.5 | 5 | | |
| Irganox 1010 | 0.5 | 0.5 | 0.5 | 0.5 |
| Cyanox LTDP | | | 0.3 | 0.3 |
| PROPERTIES | | | | |
| Rate of Remoistening & Bondability | | | | |
| Initial - % Fiber Tear/Time | 100/30 sec. | 100/30 sec. | 100/30 sec. | 100/30 sec. |
| After 24 hrs 100 F./90% RH | 100% | 100% | 100% | 100% |
| Blocking Resistance At 100 F./90% RH | Good | Good | Good | Good |
| Rate of Set | Fast | Fast | Fast | Fast |

Examples 10–13 exemplify thermoplastic compositions comprising an amorphous linear water dispersible copolyester and a crystalline water dispersible polyamide. These compositions also exhibit a fast rate of bond formation combined with good blocking resistance.

The examples comprising water dispersible copolyester in combination with a crystalline water sensitive polymer are particularly well-suited for applications such as nonwoven construction and in-line film formation in view of the fast rate of set and that the composition is tap water soluble/dispersible, body fluid insoluble, and exhibits good blocking resistance.

What is claimed is:

1. A thermoplastic composition comprising at least one crystalline water sensitive thermoplastic polymer blended with at least one amorphous water sensitive thermoplastic polymer.

2. The thermoplastic composition of claim 1 wherein the at least one crystalline water sensitive thermoplastic material is a water soluble polyamide, a water dispersible polyamide, or mixtures thereof.

3. The thermoplastic composition of claim 1 wherein the at least one amorphous water sensitive thermoplastic material is selected from the group consisting of polyvinyl alcohol, polyvinyl pyrrolidone, polyvinyl pyrrolidone/vinyl acetate, polyoxazoline, polyvinyl pyrrolidone/acrylic acid, water dispersible copolyester, amorphous water soluble polyamide, and mixtures thereof.

4. The thermoplastic composition of claim 3 wherein the at least one amorphous water sensitive thermoplastic material is a water dispersible copolyester.

5. The thermoplastic composition of claim 2 wherein the water soluble polyamide is present in an amount ranging from about 10 wt-% to about 90 wt-% in the thermoplastic composition.

6. The thermoplastic composition of claim 2 wherein the amorphous water sensitive material is present in an amount ranging from about 10 wt-% to about 90 wt-% in the thermoplastic composition.

7. The thermoplastic composition of claim 1 further comprising at least one wax in an amount up to about 30 wt-%.

8. The thermoplastic composition of claim 7 wherein the wax is polar.

9. The thermoplastic composition of claim 7 wherein the melt point of the wax is greater than about 70° C.

10. The thermoplastic composition of claim 7 wherein the melt point of the wax is greater than about 110° C.

11. The thermoplastic composition of claim 7 wherein the melt point of the wax is greater than about 140° C.

12. The thermoplastic composition of claim 1 wherein the Brookfield viscosity is less than about 2000 cPs at 177° C.

13. The thermoplastic composition of claim 1 wherein a said composition will produce a full fiber tearing bond in less than about 30 seconds.

14. The thermoplastic composition of claim 1 wherein said composition resists blocking at 90% relative humidity and 38° C.

15. The thermoplastic composition of claim 1 wherein said composition resists blocking at room temperature.

16. A remoistenable adhesive comprising:
 a) from about 10 wt-% to about 90 wt-% in the adhesive of at least one crystalline water sensitive thermoplastic polymer;
 b) from about 10 wt-% to about 90 wt-% in the adhesive of at least one amorphous water sensitive thermoplastic polymer; and
 c) up to about 30 wt-% in the adhesive of at least one wax.

* * * * *